United States Patent [19]

Lang et al.

[11] 4,409,204

[45] Oct. 11, 1983

[54] MEANS FOR THE AFTERTREATMENT OF PERMANENTLY DEFORMED HAIR

[75] Inventors: Günther Lang, Niederbeerbach; Theodor Wajaroff, Darmstadt, both of Fed. Rep. of Germany

[73] Assignee: Wella Aktiengesellschaft, Darmstadt, Fed. Rep. of Germany

[21] Appl. No.: 131,866

[22] Filed: Mar. 19, 1980

[30] Foreign Application Priority Data

Mar. 29, 1979 [DE] Fed. Rep. of Germany ....... 2912427

[51] Int. Cl.$^3$ .................... A61K 7/06; A61K 7/09; A61K 7/11
[52] U.S. Cl. .......................... 424/70; 132/7; 424/71; 424/72; 424/180
[58] Field of Search .................... 424/70, 71

[56] References Cited

FOREIGN PATENT DOCUMENTS

| | | |
|---|---|---|
| 2357158 | 5/1974 | Fed. Rep. of Germany ........ 424/71 |
| 2401795 | 7/1974 | Fed. Rep. of Germany ........ 424/71 |
| 2824025 | 6/1979 | Fed. Rep. of Germany ........ 424/70 |
| 1537672 | 7/1968 | France ................................ 424/71 |
| 2013680 | 7/1969 | France ................................ 424/71 |
| 2153075 | 4/1973 | France ................................ 424/71 |
| 46-18039 | 5/1971 | Japan ................................. 424/70 |
| 54-23135 | 2/1979 | Japan ................................. 424/70 |
| 1196021 | 6/1970 | United Kingdom ................. 424/71 |

*Primary Examiner*—Dale R. Ore
*Attorney, Agent, or Firm*—Michael J. Striker

[57] ABSTRACT

A process and composition for the aftertreatment of permanently deformed hair. Often the permanent deformation leaves reducing agent or oxidant in the hair, which leads to considerable damage to the hair. Applying to the hair a composition containing glyoxylic acid and at least one organic compound having a multiple carbon-carbon bond, containing a carboxyl group bonded to the multiple bond directly or through a methylene group, which is activated by at least one multiple CO or CN bond conjugated to that multiple bond, avoids the damage caused by permanent deformation.

6 Claims, No Drawings

MEANS FOR THE AFTERTREATMENT OF PERMANENTLY DEFORMED HAIR

BACKGROUND OF THE INVENTION

In processes as presently used for the permanent deformation of hair, the desired deformation is achieved by chemical methods. Initially, the disulfide bridges of the hair keratin are split by reduction under the influence of a suitable reducing agent. The hair is then brought into a new form and subsequently fixed in its new form by treatment with an oxidant, wherein the split disulfide compounds are bonded again. Primarily mercapto-compounds, particularly salts or derivatives of thioglycolic acid, such as ammonium thioglycolate, ammonium thiolactate and glycerin monothioglycolate are used as reducing agents, and in addition certain sulfites, preferably ammonium sulfite. Hydrogen peroxide is, primarily, used as suitable oxidant.

Subsequent to the permanent deformation, a thorough rinsing of the hair with water is done, in order to remove residues of the reducing agent and oxidant that have remained in the hair. Such residues will remain particularly when insufficient care has been taken in respect of the quantities of the reducing agent or oxidant used, when not paying exact attention to the required application period, and when there is insufficient final rinsing. Residues of the reducing agent and oxidant can, however, not be completely removed even if thorough final rinsing has been made. This is due to the characteristic of the hair keratin which will retain such residues by a rather firm bond.

Leaving such residues in the hair has an extremely disadvantageous effect upon the structure and appearance of the hair, and it will lead to considerable damage to the hair. Such damage becomes apparent particularly by the hair becoming brittle, by a reduction in the hair strength and furthermore by a decrease in the ease of combing and loss of the natural hair luster. It is to be added hereto that the durability of the permanent deformation will be reduced by residues of the reducing agent, whilst residues of the oxidant will effect an undesirable brightening of the hair coloring.

If the mercapto compounds, primarily used today, are used for the permanent deformation of hair, an unpleasant odor will furthermore by present after treatment, which can be covered by perfuming agents only with difficulty.

It was, therefore, the task of the invention, to find a means for the treatment of permanently deformed hair, by which the aforenoted disadvantages would be avoided to a great degree.

SUMMARY OF THE INVENTION

It was found heretofore that means for the aftertreatment of permanently deformed hair, with a content of
(a) glyoxylic acid, and
(b) at least one organic compound having a aliphatic multiple carbon-carbon bond, containing a carboxyl group bonded to the multiple bond directly or through a methylene group, which is activated by at least one multiple CO or CN bond conjugated to that multiple bond, are suitable to a particularly high degree for solving the task as set.

The means as per invention should particularly contain as representatives of the group (b) as noted above, such organic compounds selected from I. Compounds with activated double bond, of the general formula

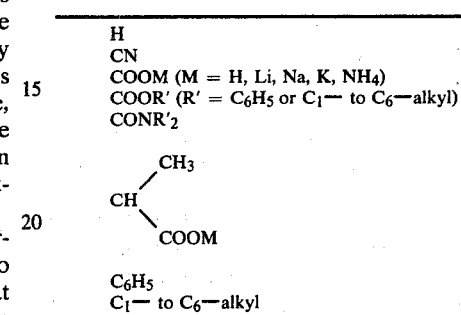

in which the substituents $R^1$, $R^2$, and $R^3$ will denote, independently of each other, one of

| |
|---|
| H |
| CN |
| COOM (M = H, Li, Na, K, NH$_4$) |
| COOR' (R' = C$_6$H$_5$ or C$_1$— to C$_6$—alkyl) |
| CONR'$_2$ |
| $CH\begin{smallmatrix}/CH_3\\ \backslash COOM\end{smallmatrix}$ |
| C$_6$H$_5$ |
| C$_1$— to C$_6$—alkyl | and wherein the substituent A constitutes one of COOM or CH$_2$COOM, and wherein M is of the significance as noted above, provided that A will signify CH$_2$COOM only when at least one of the substituents $R^1$, $R^2$, and $R^3$ will be

CN, COOM, COOR', CONR'$_2$, or

II. Compounds with the activated triple bond of the general formula $$A—C\equiv C—R^4,$$

in which the substituent $R^4$ denotes one of

| |
|---|
| H |
| CN |
| COOM (M = H, Li, Na, K, NH$_4$) |
| COOR' (R' = C$_6$H$_5$ or C$_1$— to C$_6$—alkyl) |
| CONR'$_2$ |
| $CH\begin{smallmatrix}/CH_3\\ \backslash COOM\end{smallmatrix}$ |
| C$_6$H$_5$ |
| C$_1$— to C$_6$—alkyl | and wherein the substituent A constitutes one of COOM or CH$_2$COOM, wherein M is of the significance noted above, provided that A will signify CH$_2$COOM only when the substituent $R^4$ is one of CN, COOM, COOR' or CONR'$_2$.

Examples of such suitable compounds with activated aliphatic multiple carbon-carbon bond are the aliphatic carboxylic acids
aconitic acid
acetylene dicarboxylic acid
ethylene dicarbonic acid
ethyl-maleic acid
α-ethyl-crotonic acid
i-amyl maleic acid
angelic acid n-butyl fumaric acid
n- or i-butyl maleic acid
citraconic acid
crotonic acid
fumaric acid
trans-glutaconic acid
isopropyl maleic acid
itaconic acid
maleic acid
mesaconic acid
α-methyl itaconic acid
cis-β-methyl itaconic acid
trans-α-methyl glutaconic acid
propiolic acid
cinnamic acid, the salts of these carboxylic acids with inorganic or organic bases, and, furthermore, their esters, partial esters, amides, and nitriles.

The means for aftertreatment as per invention should contain the constituents of the combination as per invention, namely (a) the glyoxylic acid and (b) the organic compounds with activated aliphatic multiple carbon-carbon bonds in a quantity of, respectively, about 0.1 to 10 percent by weight, preferably 0.2 to 3.0 percent by weight.

These means may furthermore contain additives as customary with preparations for hair cosmetics, such as, for instance ammonia, resins, oils, waxes, alcohols, wetting agents, solutes, capillary active substances, film-forming polymerisates, emulgators, thickeners, swelling agents, propellants, brighteners, fillers, colorants, perfume oils, and others.

These means for aftertreatment may be prepared in the form of a solution, a gel, a cream, or an emulsion. The means may, furthermore, be available as an aerosol or in solid form, f.i. as powder or tablets. In the latter instance however, it must be converted prior to using into one of the first-named forms of preparation, which is accomplished by the addition of a solvent. Inorganic or organic types of solvents, preferably water, or mixtures of water and lower alcohols, such as, f.i. ethanol or isopropanol, may be taken into consideration for use with the means for aftertreatment as per invention.

A particular advantage of the means as per invention consists in their ability of removing from the hair, in one step, the residues of reducing agents as well as the residues of oxidants. The chemical reactions of the two active constituents (a) the glyoxylic acid, and (b) the organic compounds with activated aliphatic multiple carbon-carbon bonds taking place herein, can be illustrated by the following exemplary reactive equations (A) Reaction of glyoxylic acid with hydrogen peroxide

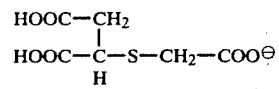

(B) Reaction of maleic acid with thioglycolate

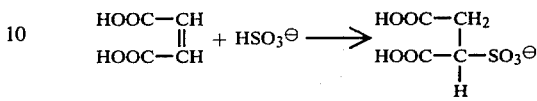

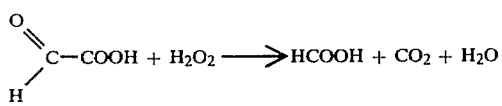

(C) Reaction of maleic acid with sulfite

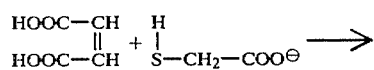

Application of the means as per invention is made in such a manner that they are applied onto the hair immediately after the permanent deformation, which may be a permanent wave or a permanent removal of curls. Generally, the means will be allowed to act upon the hair for a period between 2 and 10 minutes, and they are removed thereafter by rinsing with water. The means may, however, be allowed to remain on the hair, as, for instance, in the particular case when it is intended to provide for a simultaneous strengthening of the hair.

The novel features which are considered as characteristic for the invention are set forth in particular in the appended claims. The invention itself, however, both as to its composition and its method of operation, together with additional objects and advantages thereof, will be best understood from the following description of specific embodiments.

DESCRIPTION OF THE PREFERRED EMBODIMENTS

EXAMPLE 1

| | |
|---|---|
| 0.5 g | Glyoxylic acid monohydrate |
| 1.0 g | fumaric acid monoethylester, lithium salts |

Before using, the above powder is dissolved under stirring in 25 mL warm water. The resultant solution has a pH value of 3.2. The solution is then evenly distributed onto the hair, allowed to act for 3 to 6 minutes, and finally rinsed off with water.

EXAMPLE 2

| | |
|---|---|
| 1.0 g | glyoxylic acid monohydrate |
| 3.0 g | maleic acid |
| 0.5 g | coconut oil alcohol, ethoxylated with 10 mol ethylene oxide |
| 1.4 g | stearyl alcohol |
| 0.7 g | glycerine monostearate |
| 1.4 g | cetyl palmitate |
| 0.6 g | lauryltrimethyl ammonium chloride |
| 3.1 g | ammonia, 25% |
| 0.5 g | perfume oil |
| 87.8 g | water |
| 100.0 g | |

The pH value of this cream is 5.1. 20 g of the cream are evently distributed onto the hair and allowed to act for 3 to 6 minutes. The application time can be reduced when heat is supplied by a hood. After the required application time, the means are removed from the hair by rinsing with water.

EXAMPLE 3

| | |
|---|---|
| 0.5 g | glyoxylic acid monohydrate |
| 0.5 g | fumaric acid monoethylester, lithium salts |
| 3.0 g | polyvinylpirolidone |
| 30.0 g | isopropanol |
| 0.2 g | perfume oil |
| 0.4 g | ammonia, 25% |
| 65.4 g | water |
| 100.0 g | |

The pH value of this solution is 5.

The fumaric acid monoethylester may be replaced herein by a corresponding molar quantity of fumaric acid, maleic acid, cinnamic acid, propiolic acid, acetylene dicarboxylic acid, crotonic acid or aconitic acid. The pH value of the corresponding solutions will, depending upon the unsaturated acid used, be at between about 3 and 4.

20 ml. of the solution are evenly distributed onto the hair. Subsequently the hair is rolled onto water-wave curlers and dried under a drying hood. After removal of the curlers, the hair is then combed into a hairdo.

EXAMPLE 4

| | |
|---|---|
| 0.3 g | glyoxylic acid, monohydrate |
| 0.4 g | maleic acid |
| 1.0 g | Chitosan, with 90% free amino groups |
| 25.0 g | ethanol |
| 0.3 g | perfume oil |
| 73.0 g | water |
| 100.0 g | |

The pH value of this solution is 3.4. 20 ml. of the solution are evenly distributed onto the hair. The hair is then rolled onto water-wave curlers and dried under a drying hood. The curlers are finally removed and the hair is combed into a hairdo.

All percentages given in the present application are percent by weight.

While the invention has been illustrated and described in the preferred embodiments, it is not intended to be limited to the details shown, since various modifications may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A composition for the aftertreatment of permanently deformed hair comprising
   A. from about 0.1 to 10.0 weight percent of glyoxylic acid,
   B. from about 0.1 to 10.0 weight percent of at least one organic compound having an aliphatic multiple carbon-carbon bond selected from the group consisting of (a) a compound of the formula

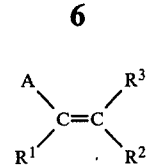

in which $R^1$, $R^2$ and $R^3$ are independently H, CN, COOM with M being H, Li, Na, K and $NH_4$, COOR' with R' being $C_6H_5$, $C_1$–$C_6$ alkyl, $CONR'_2$, and

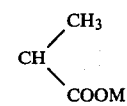

and wherein A represents COOM and $CH_2COOM$, M having the meaning noted above, provided that A signifies $CH_2COOM$ only when at least one of $R^1$, $R^2$ and $R^3$ is CN, COOM, COOR' and $CONR'_2$ and (b) a compound with an activated triple bond of the formula

$$A-C\equiv C-R^4$$

in which $R^4$ is H, CN, COOM with M being H, Li, Na, K and $NH_4$, COOR' with R' being $C_6H_5$, $C_1$–$C_6$ alkyl, $CONR'_2$, and

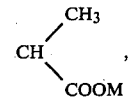

and wherein A represents COOM and $CH_2COOM$, M having the meaning noted above, provided that A signifies $CH_2COOM$ only when $R^4$ is CN, COOM, COOR', $CONR'_2$ and
   C. water.

2. A composition as recited in claim 1, wherein said glyoxylic acid is present in a quantity of about 0.2 to 3.0 percent by weight.

3. A composition as recited in claim 1, wherein said compound having a aliphatic multiple carbon-carbon bond is present in a quantity of about 0.2 to 3.0 percent by weight.

4. A composition for the aftertreatment of permanently deformed hair according to claim 1, comprising
   A. from about 0.1 to 10.0 weight percent of glyoxylic acid,
   B. from about 0.1 to 10.0 weight percent of a compound selected from the group consisting of acetylene dicarboxylic acid, aconitic acid, crotonic acid, fumaric acid, itaconic acid, maleic acid, propiolic acid and cinnamic acid, and their salts with organic or inorganic bases and
   C. water.

5. A method for the aftertreatment of permanently deformed hair, comprising evenly distributing a sufficient amount of the preparation according to claim 1 on the hair after permanent deformation, allowing said composition to act upon the hair for between about 2 and 10 minutes, followed by removing said composition by rinsing the hair with water.

6. A method for the aftertreatment of permanently deformed hair, comprising evenly distributing a sufficient amount of the preparation according to claim 1 on to the hair after permanent deformation, and allowing said composition to remain on the hair.

* * * * *